United States Patent
Arai et al.

(10) Patent No.: US 11,395,637 B2
(45) Date of Patent: Jul. 26, 2022

(54) RADIOGRAPHIC IMAGING SYSTEM AND PROGRAM

(71) Applicant: FUJIFILM Corporation, Tokyo (JP)

(72) Inventors: Takahisa Arai, Kanagawa (JP);
Takeyasu Kobayashi, Kanagawa (JP);
Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 179 days.

(21) Appl. No.: 16/788,268

(22) Filed: Feb. 11, 2020

(65) Prior Publication Data
US 2020/0261048 A1  Aug. 20, 2020

(30) Foreign Application Priority Data
Feb. 14, 2019  (JP) .............................. JP2019-024727

(51) Int. Cl.
*A61B 6/00*  (2006.01)
*A61B 6/04*  (2006.01)

(52) U.S. Cl.
CPC ............ *A61B 6/547* (2013.01); *A61B 6/0435* (2013.01); *A61B 6/4441* (2013.01); *A61B 6/4452* (2013.01)

(58) Field of Classification Search
CPC .......... A61B 6/04; A61B 6/0492; A61B 6/08; A61B 6/10; A61B 6/102; A61B 6/4258; A61B 6/4266; A61B 6/44; A61B 6/4435; A61B 6/488; A61B 6/502; A61B 6/5217; A61B 6/5229; A61B 6/5247; A61B 6/54; A61B 6/542; A61B 6/544; A61B 6/545; A61B 6/589; A61B 2576/02;
(Continued)

(56) References Cited

U.S. PATENT DOCUMENTS

2003/0161439 A1*  8/2003  Eriksson .................. A61B 6/06
378/37
2013/0345543 A1*  12/2013  Steibel, Jr. .............. A61B 6/037
600/407
(Continued)

FOREIGN PATENT DOCUMENTS

JP  2003210447  7/2003
JP  2006334020  12/2006
(Continued)

OTHER PUBLICATIONS

"Office Action of Japan Counterpart Application", dated Dec. 21, 2021, with English translation thereof, pp.1-4.

*Primary Examiner* — Anastasia Midkiff
(74) *Attorney, Agent, or Firm* — JCIPRNET

(57) ABSTRACT

A radiographic imaging system includes: a radiographic imaging apparatus body that has a movable unit and is disposed in an imaging room; a subject information acquisition unit that acquires subject information regarding a subject; a first position controller that moves a position of the movable unit to a first position according to the physique of the subject using the subject information; an imaging unit that images the subject; a recognition unit that recognizes the subject using an image of the subject captured by the imaging unit; and a second position controller that moves the position of the movable unit from the first position to a second position according to a recognition result of the recognition unit using the recognition result of the recognition unit.

17 Claims, 5 Drawing Sheets

(58) Field of Classification Search
CPC ....... G01N 2223/302; G01N 2223/306; G01N 2223/309; G01N 2223/32; G01N 2223/321; G01N 2223/323; G01N 2223/6126

See application file for complete search history.

(56) References Cited

U.S. PATENT DOCUMENTS

| | | | |
|---|---|---|---|
| 2016/0278730 A1 | 9/2016 | Moon | |
| 2017/0172531 A1* | 6/2017 | Sugiyama | ............ A61B 6/0414 |
| 2019/0285558 A1* | 9/2019 | Defreitas | ................ A61B 6/04 |

FOREIGN PATENT DOCUMENTS

| | | |
|---|---|---|
| JP | 2014012055 | 1/2014 |
| JP | 2016514538 | 5/2016 |
| WO | 2018087083 | 5/2018 |

* cited by examiner

RADIOGRAPHIC IMAGING SYSTEM AND PROGRAM

CROSS-REFERENCE TO RELATED APPLICATIONS

This application claims priority under 35 U.S.C § 119(a) to Japanese Patent Application No. 2019-024727 filed on 14 Feb. 2019. The above application is hereby expressly incorporated by reference, in its entirety, into the present application.

BACKGROUND OF THE INVENTION

1. Field of the Invention

The present invention relates to a radiographic imaging system for imaging a subject using radiation, such as X-rays, and a program for driving the radiographic imaging system.

2. Description of the Related Art

A radiographic imaging apparatus or a system for imaging a subject using radiation, such as a mammography apparatus, is known. Since each subject has a different physique or the like, the radiographic imaging system or the like usually requires adjustment according to the subject at the time of imaging.

For example, there is known a mammography apparatus that adjusts the position of a movable unit including an imaging table based on a biological index of a subject (JP2016-514538A, corresponding to US2016/278730A1). Similarly, another radiographic imaging apparatus that automatically adjusts the position of a movable unit (so-called C arm) based on the height and weight of a subject is also known (JP2003-210447A). In addition, a radiographic imaging apparatus that performs fine adjustment by manual operation according to a subject after automatically adjusting the position of a movable unit is known (JP2006-334020A).

SUMMARY OF THE INVENTION

The radiographic imaging system that automatically adjusts the position of the movable unit has a problem that its accuracy is low. This is because information regarding the subject is usually not obtained to such an extent that the position of the movable unit can be directly determined in the radiographic imaging system. For this reason, even though the position of the movable unit is automatically adjusted, it is eventually required to adjust the position of the movable unit by manual operation. Therefore, the adjustment of the position of the movable unit automatically performed by the apparatus or the system has not been sufficiently effective.

It is an object of the invention to provide a radiographic imaging system and a program capable of smoothly performing radiographic imaging by improving the accuracy of automatic position adjustment of a movable unit.

A radiographic imaging system of the invention comprises: a radiographic imaging apparatus body that has a radiation generation unit that generates radiation, a radiographic imaging unit that images a subject using the radiation, and a movable unit that supports the radiation generation unit and the radiographic imaging unit so as to be movable and that is disposed in an imaging room; a subject information acquisition unit that acquires subject information regarding the subject; a first position controller that moves a position of the movable unit to a first position according to a physique of the subject using the subject information; an imaging unit that images the subject; a recognition unit that recognizes the subject using an image of the subject captured by the imaging unit; and a second position controller that moves the position of the movable unit from the first position to a second position according to a recognition result of the recognition unit using the recognition result of the recognition unit.

It is preferable that the subject information includes information regarding the physique of the subject and/or information regarding the position of the movable unit in past radiographic imaging of the subject.

It is preferable that the position of the movable unit controlled by the first position controller and the second position controller is a height from a floor surface of the imaging room.

It is preferable that, in a case where the radiographic imaging apparatus body is a mammography apparatus, the position of the movable unit controlled by the first position controller and the second position controller is a height of an imaging table on which a breast of the subject is placed.

It is preferable that the first position controller moves the movable unit to the first position by moving the movable unit vertically upward.

It is preferable that the first position controller moves the position of the movable unit to the first position until the subject enters the imaging room after the subject information acquisition unit acquires the subject information.

It is preferable that the recognition unit determines the second position using a currently acquired recognition result of the recognition unit in a case where a difference between the current recognition result of the recognition unit and information corresponding to a recognition result of the recognition unit specified from information related to past radiographic imaging is equal to or greater than a threshold value and determines the second position used in current radiographic imaging using information related to past radiographic imaging in a case where the difference is less than the threshold value.

It is preferable that the first position controller and the second position controller move the movable unit in a case where there is no person or object within a specific range including the radiographic imaging apparatus body.

It is preferable that the specific range is at least as wide as a movable range of the movable unit.

It is preferable that the second position controller moves the movable unit at a lower speed as a distance between the radiographic imaging apparatus body and the subject becomes shorter.

It is preferable that, in a case of moving the movable unit vertically downward, the first position controller and the second position controller move the movable unit at a lower speed than that in a case of moving the movable unit vertically upward.

It is preferable that the recognition unit recognizes the physique of the subject.

It is preferable that the recognition unit recognizes at least a height of the subject and determines the second position using at least the height of the subject.

It is preferable that the recognition unit recognizes a part of the subject to be imaged using the radiation.

It is preferable that the recognition unit recognizes an examination technician who uses the radiographic imaging apparatus body so as to be distinguished from the subject.

It is preferable that, in a case where radiographic imaging is performed with the second position as the position of the movable unit, registering the second position in the subject information is proposed.

A program of the invention is a program for driving a radiographic imaging system having a movable unit that supports a radiation generation unit and a radiographic imaging unit so as to be movable. The program causes an arithmetic device included in the radiographic imaging apparatus body or an arithmetic device cooperating with the radiographic imaging apparatus body to determine the position of the movable unit using a learned model for outputting the position of the movable unit according to a subject based on an input of an image obtained by imaging the subject.

The radiographic imaging system and the program of the invention can smoothly perform radiographic imaging by improving the accuracy of automatic position adjustment of the movable unit.

DESCRIPTION OF THE PREFERRED EMBODIMENTS

First Embodiment

Figure 1:
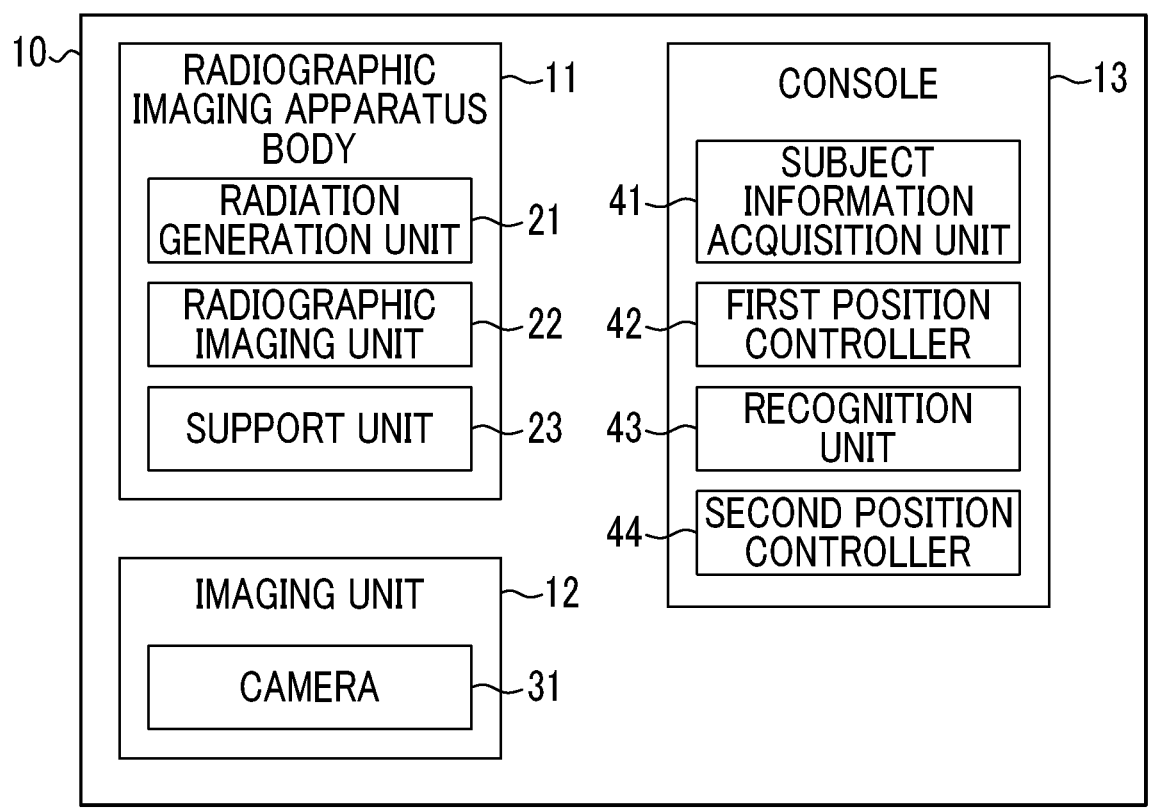
FIG. 1 is a block diagram of a radiographic imaging system.

As shown in FIG. 1, a radiographic imaging system 10 comprises a radiographic imaging apparatus body 11 for imaging a subject 18 (refer to FIG. 2) using radiation, a console 13 for controlling the radiographic imaging apparatus body 11, and an imaging unit 12 that images the subject 18 and the like using light other than radiation, such as visible light, ultraviolet light, or infrared light. These are connected to each other by a cable or wirelessly, so that data, control signals, and the like are transmitted and received therebetween as necessary.

Figure 2:
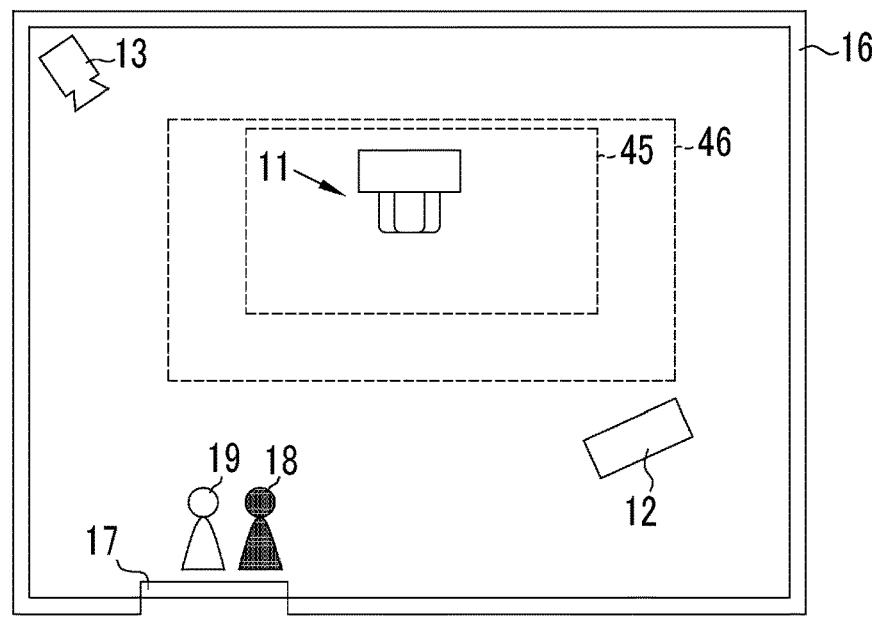
FIG. 2 is an explanatory diagram showing the configuration of the radiographic imaging system.

As shown in FIG. 2, at least the radiographic imaging apparatus body 11 is disposed in an imaging room 16. The imaging room 16 is a room for performing radiographic imaging. In the present embodiment, the imaging unit 12 and the console 13 are also provided in the imaging room 16. The imaging room 16 has, for example, a sliding door 17 as an entrance. Therefore, in the case of imaging the subject 18 using the radiographic imaging system 10, the subject 18 and an examination technician (hereinafter, referred to as a radiology technician) 19 who uses (operates) the radiographic imaging apparatus body 11 enters the imaging room 16 through the door 17.

The radiographic imaging apparatus body 11 comprises a radiation generation unit 21, a radiographic imaging unit 22, and a support unit 23 (refer to FIG. 1). The radiation generation unit 21 generates radiation, such as X-rays. In a case where the radiation generation unit 21 generates X-rays, the radiation generation unit 21 is an X-ray tube or a mono tank in which an X-ray tube, other circuits, and the like are integrated. The radiographic imaging unit 22 is a radiation detector that images the subject 18 using radiation transmitted through the subject 18. The radiographic imaging unit 22 is, for example, a flat panel detector (FPD). The support unit 23 supports the radiation generation unit 21 and the radiographic imaging unit 22 movably. The support unit 23 is, for example, a C-shaped arm (so-called C arm) or the like. The support unit 23 that supports the radiation generation unit 21 and the radiographic imaging unit 22 (all of the radiation generation unit 21, the radiographic imaging unit 22, and the support unit 23) is a movable unit, which adjusts a position in the case of imaging the subject 18 using radiation, in the radiographic imaging apparatus body 11.

The imaging unit 12 is configured using one or a plurality of cameras 31. The camera 31 is, for example, a digital camera or a digital video camera that performs imaging using visible light or infrared light. In the imaging unit 12, the camera 31 provided in the imaging room 16 images the door 17 that is the entrance of the imaging room 16 and the vicinity thereof, a movable range 45 (refer to FIG. 2) of the radiographic imaging apparatus body 11, and a safety range 46 (refer to FIG. 2). The reason why the camera 31 provided in the imaging room 16 images the door 17 and the vicinity thereof is to image the subject 18 and/or the radiology technician 19. The camera 31 provided in the imaging room 16 images the movable range 45 and the safety range 46 of the radiographic imaging apparatus body 11 for safety. The safety range 46 is a range in which there should be no person or object in the case of operating the radiographic imaging system 10, and usually includes the radiographic imaging apparatus body 11 and the movable range 45 of the radiographic imaging apparatus body 11. That is, since the safety range 46 is set to be wider than the movable range 45 of the radiographic imaging apparatus body 11, the imaging of the safety range 46 also serves as the imaging of the movable range 45 of the radiographic imaging apparatus body 11.

Among the cameras 31 configuring the imaging unit 12, those for imaging the subject 18 and/or the radiology technician 19 can be provided in an examination room, a waiting room, a passage leading to the imaging room 16, and the like in addition to the imaging room 16 or instead of being provided in the imaging room 16.

The console 13 comprises a subject information acquisition unit 41, a first position controller 42, a recognition unit 43, and a second position controller 44 (refer to FIG. 1). In addition, the console 13 comprises a display unit (a monitor or the like) (not shown) and an operation unit, such as a keyboard or a pointing device.

The subject information acquisition unit 41 acquires subject information that is information regarding the subject 18. The subject information acquired by the subject information acquisition unit 41 includes information regarding the physique of the subject 18, information regarding the imaging part of the subject 18, and/or information regarding the past radiographic imaging of the subject. The information regarding the physique of the subject 18 is, for example, information indicating the physique dimensions of the subject 18, such as the height of the subject 18. The information regarding the past radiographic imaging is information related to specific embodiments of other radiographic imaging, such as the position (height) of the movable unit 70, the compression force of a compression plate 66, the thickness of the breast compressed by the compression plate 66, X-ray quality, and/or X-ray dose, in the past radiographic imaging of the subject. In the present embodiment, the subject information acquisition unit 41 acquires at least the height of the subject 18. This is because the information can be used in the case of automatically adjusting the position of the movable unit. In addition, the information regarding the imaging part of the subject 18 is the name of the imaging part and/or the position of the imaging part. The imaging part is a part of the subject imaged using radiation.

In a case where the information regarding the physique of the subject (physique information) and the information regarding the past radiographic imaging are stored in the radiographic imaging system 10, these pieces of information are referred to. In a case where the information regarding the physique of the subject (physique information) and the information regarding the past radiographic imaging are not stored in the radiographic imaging system 10, these pieces of information can be acquired from systems that are directly or indirectly linked to the radiographic imaging system 10, such as a radiology information system (so-called RIS), a hospital information system (so-called HIS), and a picture archiving and communication system (PACS). For example, the subject information acquisition unit 41 can acquire the information regarding the physique of the subject included in the electronic medical record by acquiring the electronic medical record from the electronic medical record server included in the hospital information system. In addition, the subject information acquisition unit 41 can acquire the information regarding the past radiographic imaging from the electronic medical record, and can also acquire the information regarding the past radiographic imaging, which is recorded together with the radiographic image, by acquiring the radiographic image from the PACS.

The first position controller 42 moves the position of the movable unit to a first position according to the physique of the subject 18 using subject information. That is, the first position controller 42 automatically adjusts the position of the movable unit. The timing at which the first position controller 42 adjusts the position of the movable unit is, for example, a timing before the subject 18 enters the imaging room 16 or a timing until the subject 18 approaches the radiographic imaging apparatus body 11 by a predetermined distance or shorter after the subject 18 enters the imaging room 16 (for example, until the subject 18 enters the safety range 46). In the present embodiment, the first position controller 42 moves the position of the movable unit to the first position until the subject 18 enters the imaging room 16 after the subject information acquisition unit 41 acquires the subject information. In particular, this is for smooth imaging or preparation for imaging.

The recognition unit 43 recognizes the subject 18 using an image (or a video that is a set of images; the same hereinbelow) of the subject 18 captured by the imaging unit 12. In addition, the recognition unit 43 recognizes the radiology technician 19 using an image captured by the imaging unit 12 (hereinafter, referred to as a camera image). This is to prevent erroneous adjustment of the position of the movable unit due to misrecognition of the subject 18 and the radiology technician 19 by recognizing the subject 18 and the radiology technician 19 so that the subject 18 and the radiology technician 19 who enter the imaging room 16 are distinguished from each other. The recognition of the subject 18 refers to obtaining the information regarding the physique of the subject 18 and/or the information regarding the imaging part so that the subject 18 is distinguished from other persons, such as the radiology technician 19. In the present embodiment, the recognition unit 43 recognizes the physique of the subject 18. More specifically, the recognition unit of the present embodiment recognizes at least the height of the subject 18. The radiology technician 19 registers the face and the like in the console 13 (recognition unit 43) and the like. For this reason, the recognition unit 43 recognizes a person other than the radiology technician 19 as the subject 18.

In addition, the recognition unit 43 can recognize whether or not there is a person or an object in the movable range 45 and/or the safety range 46 of the radiographic imaging apparatus body 11 using a camera image.

The recognition unit 43 outputs a recognition result regarding the subject 18 to the second position controller 44. The recognition result of the recognition unit 43 is information regarding the physique of the subject 18 and/or information regarding the imaging part of the subject 18 or position information of the movable unit determined using the information regarding the physique of the subject 18 and/or the information regarding the imaging part of the subject 18 (specifically, a value of a second position that the second position controller 44 uses as a control target of the movable unit). That is, the recognition unit 43 not only can simply obtain the information regarding the physique of the subject 18 and/or the information regarding the imaging part using a camera image but also can determine and output the position information of the movable unit as an adjustment target using the information regarding the physique of the subject 18 and/or the information regarding the imaging part.

In a case where the difference between the current recognition result of the recognition unit 43 and "information corresponding to the recognition result of the recognition unit 43" specified from information related to the past radiographic imaging is equal to or greater than a threshold value (first threshold value), the recognition unit 43 can determine the second position using the currently acquired recognition result of the recognition unit 43. In a case where the difference between the current recognition result of the recognition unit 43 and the "information corresponding to the recognition result of the recognition unit 43" specified from information related to the past radiographic imaging is less than the threshold value, the recognition unit 43 can determine the second position used in the current radiographic imaging using the information in the past radiographic imaging. This is because radiographic imaging can be more smoothly performed by shortening the time required to determine the second position in the case of determining the second position using the information regarding the past radiographic imaging. The information related to the past radiographic imaging is the recognition result of the recognition unit 43 in the past radiographic imaging (for example, the second position in the past radiographic imaging), the position (height) of the movable unit 70 in the past radiographic imaging, and the like. The information related to the past radiographic imaging can be acquired as necessary by storing the information related to the past radiographic imaging in the radiographic imaging system 10, for example. In addition, the information related to the past radiographic imaging can be automatically acquired from a system linked to the radiographic imaging system 10 (for example, an electronic medical record stored in an electronic medical record server), or can be acquired by manual input of the radiology technician 19 or the like.

The second position controller 44 moves the position of the movable unit from the first position to the second position according to the recognition result of the recognition unit 43 using the recognition result of the recognition unit 43. In a case where the recognition unit 43 outputs the information regarding the physique of the subject 18 and/or the information regarding the imaging part of the subject 18 as a recognition result, the second position controller 44 determines the second position using the information. In a case where the recognition unit 43 outputs the information of the second position as a recognition result, the movable unit is moved to the second position using the information of the second position.

Figure 3:
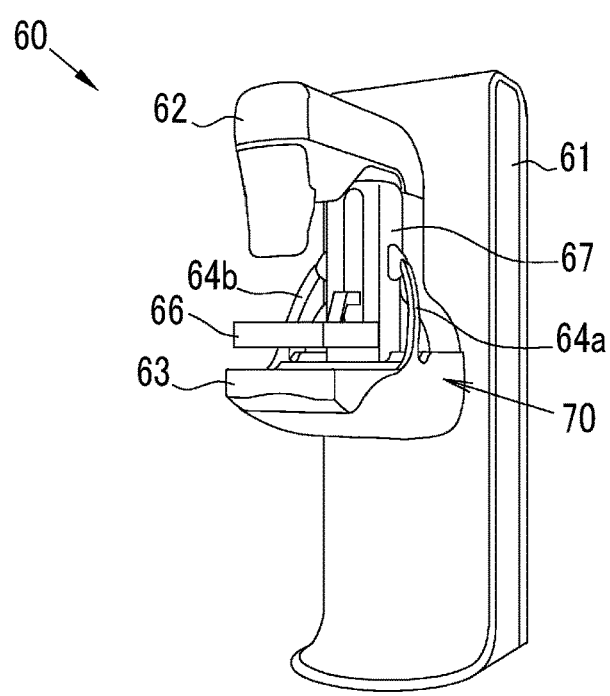
FIG. 3 is an external view of a mammography apparatus.

In the present embodiment, the radiographic imaging apparatus body 11 is a mammography apparatus 60. As shown in FIG. 3, the mammography apparatus 60 comprises a support 61, an X-ray generation unit 62 that is the radiation generation unit 21, an imaging table 63 in which the radiographic imaging unit 22 is provided, the compression plate 66, an elevating unit 67, and the like. The mammography apparatus 60 is an X-ray imaging apparatus for imaging the breast of the subject 18 using X-rays. The X-ray generation unit 62 and the imaging table 63 are integrated to form a movable unit 70 that performs position adjustment according to the subject 18 in the mammography apparatus 60. Therefore, the support unit 23 in the mammography apparatus 60 is a housing (the entire movable unit 70) for integrating the X-ray generation unit 62 and the imaging table 63.

The imaging table 63 is a stage on which the breast of the subject 18 is placed, and the breast of the subject 18 is interposed between the imaging table 63 and the compression plate 66 at the time of imaging. In addition, a gripping unit 64a that the subject 18 grips with the right hand and a gripping unit 64b that the subject 18 grips with the left hand are attached to the imaging table 63. The gripping unit 64a and the gripping unit 64b are so-called armrests.

The compression plate 66 compresses the breast of the subject 18 placed on the imaging table 63 to make the breast flat. This is to reduce the overlap of normal mammary glands so that it becomes easy to find a lesion clearly in a case where there is a lesion. The elevating unit 67 moves the compression plate 66 up and down with respect to the imaging table 63. In this manner, the elevating unit 67 supports the compression plate 66 almost in parallel to the imaging table 63 and at a specific distance according to the thickness of the breast.

Figure 4:
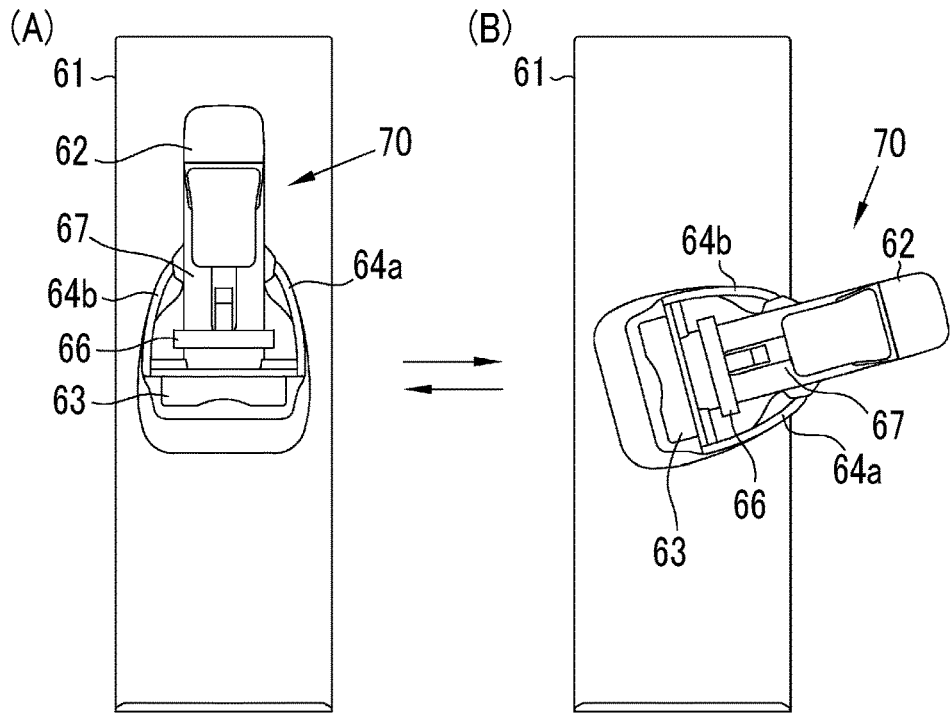
FIG. 4 is an explanatory diagram showing how a movable unit moves.

As shown in FIG. 4, the movable unit 70 can freely rotate within a predetermined angle range while maintaining the relative position and direction of the X-ray generation unit 62 and the imaging table 63. Therefore, the mammography apparatus 60 can perform imaging in a state in which the imaging table 63 is horizontally disposed or the imaging table 63 is disposed so as to be inclined from the horizontal plane. Specifically, as shown in (A) of FIG. 4, the mammography apparatus 60 can perform craniocaudal imaging (CC imaging) for imaging the breast from the head-to-tail direction by arranging the imaging table 63 in the horizontal direction. In addition, as shown in (B) of FIG. 4, the mammography apparatus 60 can perform mediolateral oblique imaging (MLO imaging) for imaging the breast from the internal and external oblique directions by arranging the imaging table 63 so as to be inclined. Although not shown, the mammography apparatus 60 can rotate the imaging table 63 and the like in a direction opposite to that in (B) of FIG. 4.

Figure 5:
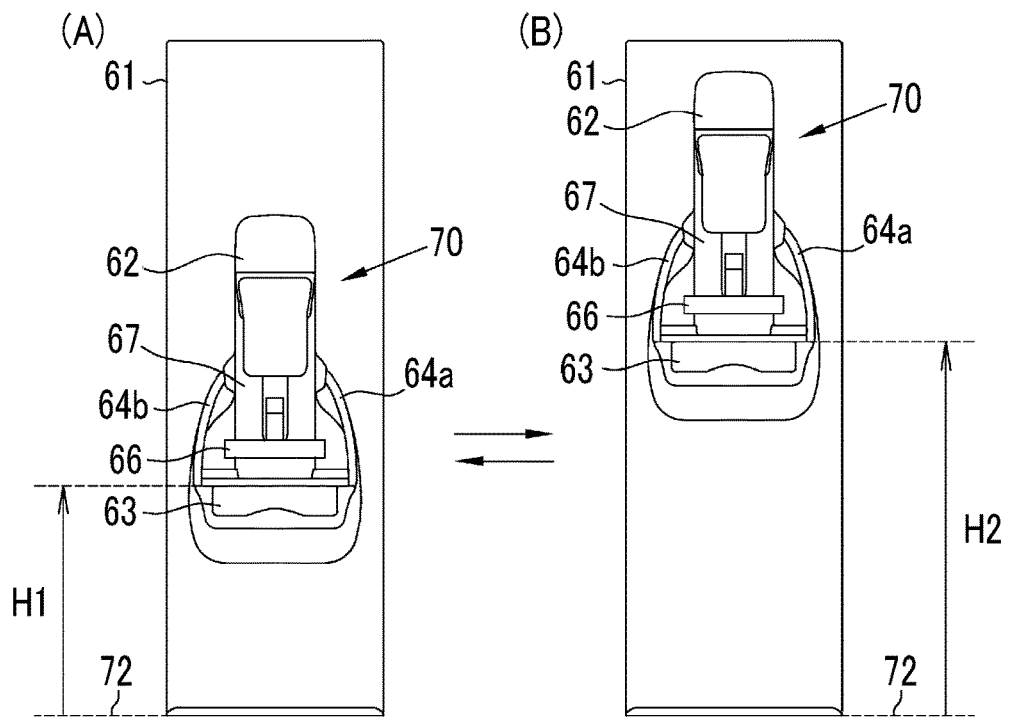
FIG. 5 is an explanatory diagram showing how a movable unit moves.

As shown in FIG. 5, the movable unit 70 can freely move in the vertical direction while maintaining the relative position and direction of the X-ray generation unit 62 and the imaging table 63. Therefore, the mammography apparatus 60 can perform imaging with a comfortable posture by adjusting the position of the imaging table 63 or the like according to the physique of the subject 18. In the mammography apparatus 60, the position of the movable unit 70 in the vertical direction is the height of the imaging table 63 with respect to a floor surface 72 (ground surface of the support 61) of the imaging room 16, and can be freely adjusted within the range of a minimum height H1 shown in (A) of FIG. 5 and a maximum height H2 shown in (B) of FIG. 5.

Figure 6:
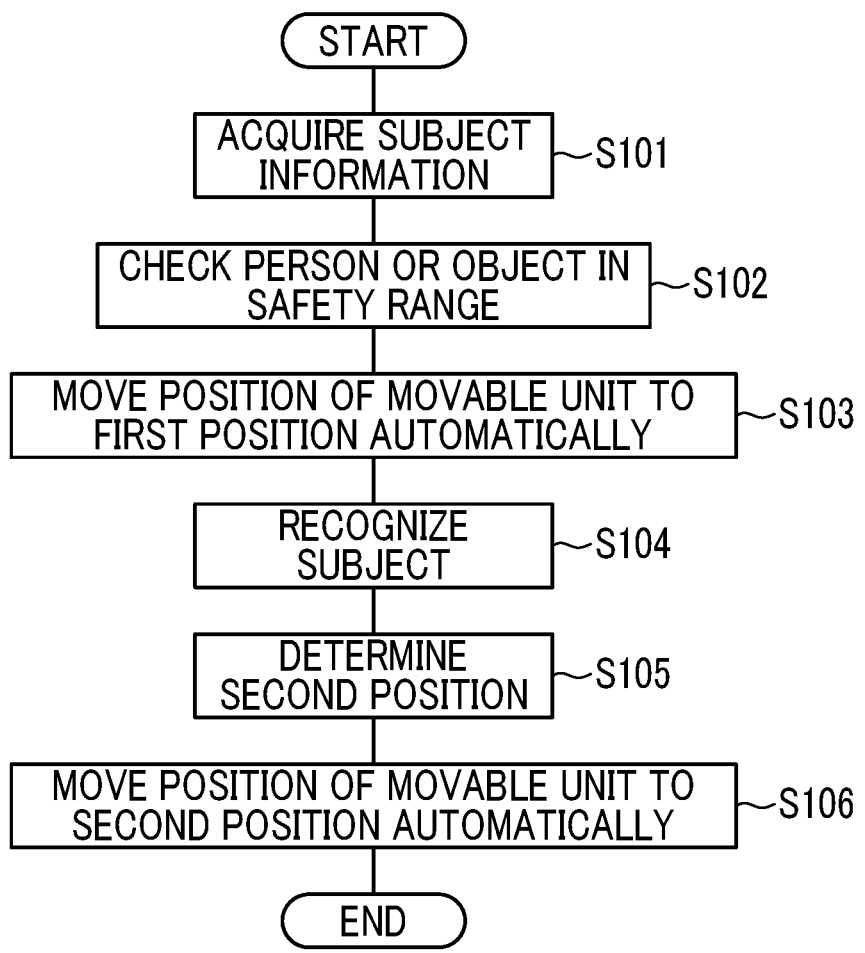
FIG. 6 is a flowchart relevant to the position adjustment of a movable unit.

Hereinafter, an operation of automatically adjusting the movable unit 70 by the radiographic imaging system 10, which is configured using the mammography apparatus 60 as described above, will be described. As shown in FIG. 6, in a case where an imaging request for the specific subject 18 is received, the console 13 acquires subject information related to the subject 18 using the subject information acquisition unit 41 (step S101). Here, the height data of the subject 18 is acquired.

In a case where the subject information acquisition unit 41 acquires the subject information, the recognition unit 43 recognizes a person or an object in the safety range 46 using an image obtained by imaging the safety range 46 with the camera 31 of the imaging unit 12. In this manner, the console 13 checks a person or an object in the safety range 46 (step S102). In a case where a person or an object is found in the safety range 46, automatic adjustment of the position of the movable unit 70 is not performed, and for example, a warning indicating the fact is provided. This is for safety.

In a case where there is no person or object in the safety range 46, the process proceeds to a step of automatically adjusting the position of the movable unit 70. That is, the first position controller 42 moves the position of the movable unit 70 to the first position according to the height of the subject 18 (step S103). That is, a rough position is temporarily determined before position adjustment to the second position to be performed later.

Thereafter, in a case where the subject 18 and the radiology technician 19 enter the imaging room 16, the imaging unit 12 images the subject 18 and the radiology technician 19 near the door 17 using the camera 31, and the recognition unit 43 recognizes the subject 18 using the image (camera image) (step S104). Here, the recognition unit 43 recognizes the height of the subject 18, the height of the breast as an imaging part from the floor surface 72, and the like. More specifically, the recognition unit 43 specifies the subject 18 so as to be distinguished from the radiology technician 19 using the camera image. Thereafter, the recognition unit 43 calculates the physique (dimensions) of the subject, such as the height of the subject 18 and the height of the breast, using the camera image. Then, the recognition unit 43 calculates the position (second position) of the movable unit 70 that matches the more actual situation (dimensions such as physique) of the subject 18 using the height of the subject 18, the height of the breast, and the like that have been recognized using the camera image (step S105), and inputs the result to the second position controller 44. Then, the second position controller 44 automatically adjusts the position of the movable unit 70 from the temporary first position of the movable unit 70 to the determined second position (step S106).

As described above, the radiographic imaging system 10 temporarily adjusts the position of the movable unit 70 to the first position using the subject information, and then automatically adjusts the position of the movable unit 70 to the second position that matches the more actual situation of the subject 18 using the actually captured subject image. Therefore, according to the radiographic imaging system 10, in a case where the subject 18 reaches the mammography apparatus 60 (radiographic imaging apparatus body 11), it is possible to automatically adjust the position of the movable unit 70 with high accuracy to such an extent that adjustment by manual operation is unnecessary or extremely small. As a result, radiographic imaging can be smoothly performed.

Since the radiographic imaging system 10 adjusts the position of the movable unit 70 according to the actually recognized subject 18 using a camera image, it is possible to accurately adjust the position of the movable unit 70 even for the subject 18 who is to be imaged for the first time. In addition, the radiographic imaging system 10 recognizes the subject 18 using a camera image, calculates physique dimensions such as the height of the subject 18, and determines the position (second position) of the movable unit 70 according to the calculated height and the like, thereby being able to adjust the position of the movable unit 70 according to the actually recognized subject 18. Therefore, even in a case where there are temporary or continuous changes in the physique of the subject 18, such as a case where the subject 18 uses a wheelchair, it is possible to accurately adjust the position of the movable unit 70.

According to the radiographic imaging system 10, even in a case where adjustment to the second position cannot be performed, such as a case where an abnormality occurs in the camera 31, the movable unit 70 can be automatically adjusted at least up to the temporarily determined first position. Therefore, the position adjustment width of the movable unit 70 by manual operation is small. For this reason, imaging can be smoothly performed.

In the embodiment described above, it is preferable that the radiographic imaging system 10 automatically returns the position of the movable unit 70 to the minimum height H1 after completing the imaging and the first position controller 42 moves the movable unit 70 vertically upward to move the movable unit 70 to the first position. This is to reliably prevent problems, such as a person or an object being caught between the movable unit 70 and the floor surface 72.

In addition, it is preferable that the first position controller 42 and the second position controller 44 move the movable unit 70 in a case where there is no person or object within a specific range including the radiographic imaging apparatus body 11. This is for safety. The specific range referred to herein is, for example, the movable range 45 or the safety range 46, but is preferably at least as wide as the movable range 45 of the movable unit 70. This is also for safety.

In the embodiment described above, it is preferable that the second position controller 44 moves the movable unit 70 at a lower speed as the distance between the radiographic imaging apparatus body 11 and the subject 18 becomes shorter. This is particularly for safety considerations since the adjustment of the position of the movable unit 70 to the second position is performed after the subject 18 enters the imaging room 16. In the case of moving the movable unit 70 vertically downward, it is preferable that the first position controller 42 and the second position controller 44 move the movable unit 70 at a lower speed than that in the case of moving the movable unit 70 vertically upward. This is to reduce problems, such as a person or an object being caught between the movable unit 70 and the floor surface 72, even in a case where a person or an object inevitably passes between the movable unit 70 and the floor surface 72.

In the embodiment described above, the recognition unit 43 recognizes the height of the subject 18 and the height of the breast as an imaging part from the floor surface 72 using a camera image. However, also in a case where the recognition unit 43 recognizes only one of the height of the subject 18 and the imaging part, the radiographic imaging system 10 has the above-described effect. That is, the recognition unit 43 can recognize only the height of the subject 18 and determine the second position using only the height of the subject 18. In this case, as in a case where the radiographic imaging apparatus body 11 is the mammography apparatus 60, the second position can be quickly and accurately determined regardless of the subject 18 in a case where the imaging part is determined. Therefore, is easy to perform imaging smoothly.

Second Embodiment

In the first embodiment described above, the first position controller 42 moves the movable unit 70 to the first position based on the height of the subject 18 that is the subject information acquired by the subject information acquisition unit 41. However, in a case where the subject information acquisition unit 41 acquires "information regarding the past imaging of the subject" as subject information, it is preferable to determine the first position using the "information regarding the past imaging of the subject". This is because adjustment to the second position is easy (in some cases, adjustment is not necessary) in a case where the first position that is the temporarily determined position of the movable unit 70 is accurate and accordingly the positioning of the movable unit 70 can be completed particularly quickly and accurately, so that radiographic imaging can be performed particularly smoothly. In addition, even in a case where recognition processing using a camera image is not possible or malfunctioning, such as a case where the imaging unit 12 breaks down so that no camera image can be acquired, a case where the imaging unit 12 cannot capture the subject 18, a case where the recognition unit 43 cannot recognize the subject 18 satisfactorily, or a case where the recognition unit 43 cannot recognize the physique and the like of the subject 18 satisfactorily (height and the like cannot be calculated), the movable unit 70 can be moved to the almost accurate first position. Therefore, it is possible to smoothly perform radiographic imaging.

Figure 7:
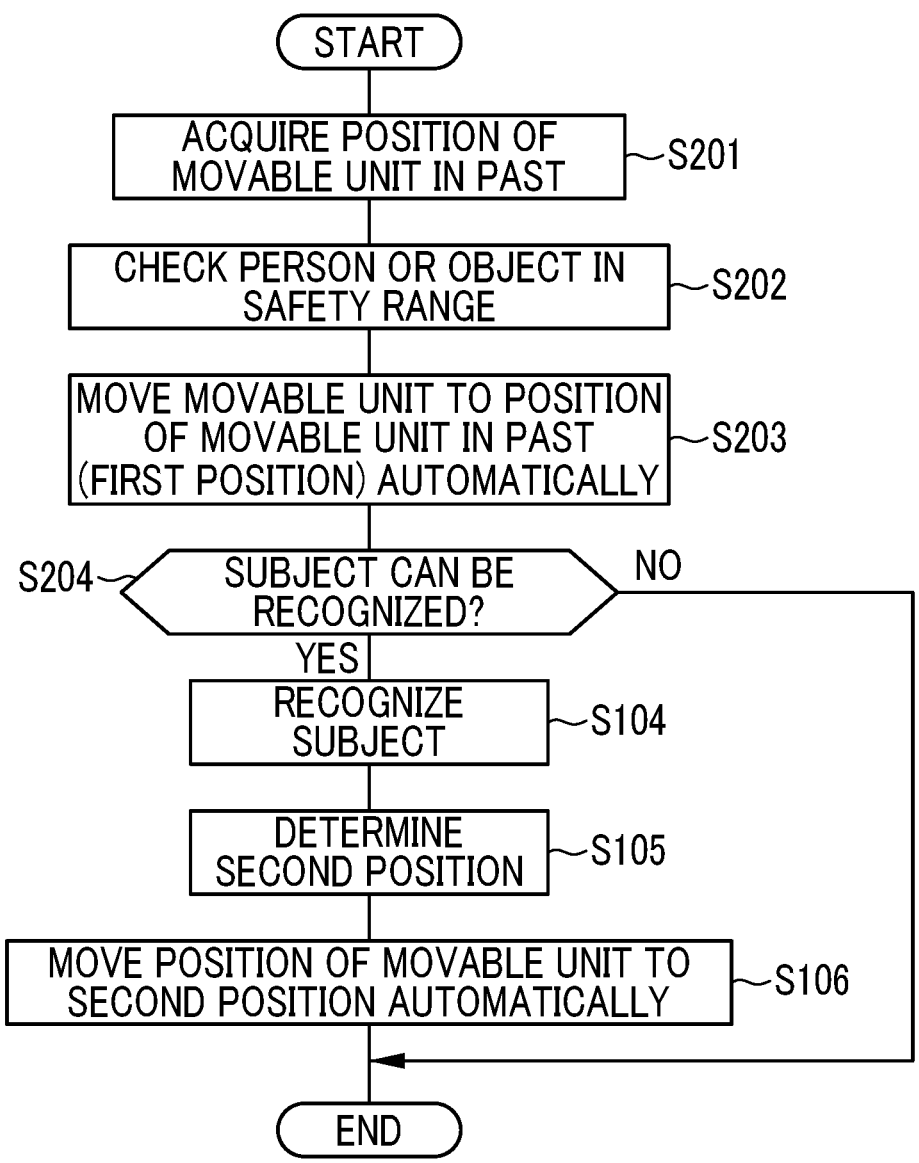
FIG. 7 is a flowchart of a second embodiment.

For example, as shown in FIG. 7, the subject information acquisition unit 41 acquires the position of the movable unit 70 in the past radiographic imaging of the subject 18 as subject information (step S201). Thereafter, the presence or absence of a person or an object within the safety range 46 is checked using a camera image (step S202), and the first position controller 42 determines the position of the movable unit 70 in the past radiographic imaging as the first position. As a result, the first position controller 42 automatically moves the movable unit 70 to the position of the movable unit 70 in the past radiographic imaging (step S203).

Thereafter, in a case where there is no malfunction in the imaging unit 12 and the recognition unit 43 and the subject 18 can be recognized using a camera image (step S204: YES), the recognition unit 43 recognizes the subject 18 (step S104) and determines the second position (step S105), and the second position controller 44 adjusts the movable unit 70 to the second position (step S106). On the other hand, in a case where there is a malfunction in the imaging unit 12 or the recognition unit 43 (step S204: NO), the processing for recognizing the subject 18, the second position determination processing, the adjustment of the position of the movable unit 70 to the second position, and the like are not performed and the imaging instruction is awaited. In this case, the radiology technician 19 can manually adjust the position of the movable unit 70 as necessary.

In the above-described first and second embodiments, modification examples thereof, and the like, in a case where the position of the movable unit 70 is automatically adjusted to the second position to perform radiographic imaging, the console 13 preferably proposes that the radiology technician 19 registers the second position in the subject information. This is because the second position registered in the next imaging becomes the first position in the above-described embodiment in a case where the second position used in the current imaging is registered, so that the accuracy of the position adjustment of the movable unit 70 is further improved. The method for the console 13 to propose that the second position is registered in the subject information is, for example, notification of a message using text or voice. However, in a case where the difference between the second position in the current imaging and the second position in the past radiographic imaging is equal to or greater than a predetermined threshold value (second threshold value), it is preferable not to propose not registering the second position in the current imaging or to selectively propose whether or not to register the second position in the current imaging. This is because, in a case where the subject 18 temporarily uses a wheelchair and there is a change in the physique, it reduces the position adjustment width of the movable unit 70 not to use the second position in the current imaging in the next imaging, so that it is possible to smoothly perform the imaging.

The subject information related to the second position may be stored (registered) in the radiographic image as information attached to the captured radiographic image or so as to be associated with the radiographic image. In addition, the subject information related to the second position may be stored in the radiographic imaging system 10 and the radiographic imaging apparatus body 11 (mammography apparatus 60).

In the above-described first and second embodiments, modification examples thereof, and the like, in a case where the recognition unit 43 outputs the information of the second position to the second position controller 44, the recognition unit 43 can be configured using a program that causes an arithmetic device (a CPU, a GPU, a memory, or a combination thereof) included in the radiographic imaging apparatus body 11 or an arithmetic device cooperating with the radiographic imaging apparatus body 11 to determine the position of the movable unit 70 using a learned model for outputting the position of the movable unit 70 according to the subject 18 based on the input of an image obtained by imaging the subject (camera image captured by the camera 31). That is, the recognition unit 43 can be configured using an artificial intelligence (AI) program that outputs the second position based on the input of a camera image.

In the above-described first and second embodiments, modification examples thereof, and the like, the hardware structures of processing units for executing various kinds of processing, such as the subject information acquisition unit 41, the first position controller 42, the recognition unit 43, and the second position controller 44, are various processors shown below. The various processors include a central processing unit (CPU) that is a general-purpose processor that executes software (program) to function as various processing units, a programmable logic device (PLD) that is a processor whose circuit configuration can be changed after manufacture, such as a graphical processing unit (GPU) and a field programmable gate array (FPGA), and a dedicated electric circuit that is a processor having a circuit configuration that is designed for exclusive use in order to execute various kinds of processing.

In the above-described first and second embodiments, modification examples thereof, and the like, the radiographic imaging system 10 comprises the mammography apparatus 60 as the radiographic imaging apparatus body 11. However, the radiographic imaging system 10 according to the embodiment of the invention also has a movable unit in addition to the mammography apparatus 60. Therefore, the radiographic imaging system 10 according to the embodiment of the invention is also suitable for a case where a radiographic imaging apparatus that requires position adjustment (including direction adjustment) according to the subject 18 is provided.

One processing unit may be configured by one of various processors, or may be a combination of two or more processors of the same type or different types (for example, a combination of a plurality of FPGAs, a combination of a CPU and an FPGA, or a combination of a CPU and a GPU). Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: radiographic imaging system
11: radiographic imaging apparatus body
12: imaging unit
13: console
16: imaging room
17: door
18: subject
19: radiology technician (examination technician)
21: radiation generation unit
22: radiographic imaging unit
23: support unit
31: camera
41: subject information acquisition unit
42: first position controller
43: recognition unit
44: second position controller
45: movable range
46: safety range
60: mammography apparatus
61: support
62: X-ray generation unit
63: imaging table
64a: gripping unit
64b: gripping unit
66: compression plate
67: elevating unit
70: movable unit
72: floor surface
S101 to S204: operation step

What is claimed is:

1. A radiographic imaging system, comprising:
   a radiographic imaging apparatus body disposed in an imaging room and having radiation generation unit that generates radiation, a radiographic imaging unit that images a subject using the radiation, and a movable unit that movably supports the radiation generating unit and the radiographic imaging unit;
   a camera that captures an image of the subject by using light other than the radiation; and
   a processor configured to:
      acquire subject information regarding the subject;
      perform a first position control in which a position of the movable unit is automatically moved to a first position according to a physique of the subject using the subject information;
      recognize the subject using the image of the subject captured by the camera; and
      perform a second position control in which the position of the movable unit is moved from the first position to a second position automatically according to the recognition result, wherein the processor determines the second position using a currently acquired recognition result of the processor in a case where a difference between the current recognition result of the processor and information corresponding to a recognition result of the processor specified from information related to past radiographic imaging is equal to or greater than a threshold value, and determines the second position used in current radiographic imaging using information related to past radiographic imaging in a case where the difference is less than the threshold value.

2. The radiographic imaging system according to claim 1, wherein the subject information includes information regarding the physique of the subject and/or information regarding the position of the movable unit in past radiographic imaging of the subject.

3. The radiographic imaging system according to claim 1, wherein the position of the movable unit controlled in the first position control and the second position control is a height from a floor surface of the imaging room.

4. The radiographic imaging system according to claim 2, wherein, in a case where the radiographic imaging apparatus body is a mammography apparatus, the position of the movable unit controlled in the first position control and the second position control is a height of an imaging table on which a breast of the subject is placed.

5. The radiographic imaging system according to claim 1, wherein during the first position control, the movable unit is moved vertically upward to the first position.

6. The radiographic imaging system according to claim 1, wherein in the first position control, after the subject information acquisition unit acquires the subject information, the position of the movable unit is moved to the first position until the subject enters the imaging room.

7. The radiographic imaging system according to claim 1, wherein during the first position control and second position control, the movable unit is moved in a case where there is no person or object within a specific range including the radiographic imaging apparatus body.

8. The radiographic imaging system according to claim 7, wherein the specific range is at least as wide as a movable range of the movable unit.

9. The radiographic imaging system according to claim 1, wherein during the second position control, the movable unit is moved at a lower speed as a distance between the radiographic imaging apparatus body and the subject becomes shorter.

10. The radiographic imaging system according to claim 1, wherein, in a case of moving the movable unit vertically downward, during the first position control and the second position control, the movable unit is moved at a lower speed than that in a case of moving the movable unit vertically upward.

11. The radiographic imaging system according to claim 1, wherein the processor recognizes the physique of the subject.

12. The radiographic imaging system according to claim 11, wherein the processor recognizes at least a height of the subject, and determines the second position using at least the height of the subject.

13. The radiographic imaging system according to claim 1, wherein the processor recognizes a part of the subject, wherein the part of the subject is captured by the camera and is to be imaged using the radiation.

14. The radiographic imaging system according to claim 1, wherein the processor recognizes an examination technician who uses the radiographic imaging apparatus body so as to be distinguished from the subject.

15. The radiographic imaging system according to claim 1, wherein, in a case where radiographic imaging is performed with the second position as the position of the movable unit, the processor is further configured to register the second position in the subject information.

16. A non-transitory device-readable medium for storing a device-executable program for driving a radiographic imaging system having a radiation generation unit that generates radiation, a radiographic imaging unit that images a subject using the radiation, and a movable unit that movably supports the radiation generation unit and a radiographic imaging unit, a camera that images the subject using light other than the radiation, and a processor in which the device-executable program is loaded causing the radiographic imaging apparatus body to execute:
   acquiring subject information regarding the subject;
   performing a first position control in which a position of the movable unit is automatically moved to a first position according to a physique of the subject using the subject information;
   recognizing the subject using the image of the subject captured by the camera; and
   performing a second position control in which the position of the movable unit is moved from the first position to a second position automatically according to the recognition result, wherein the processor determines the second position using a currently acquired recognition result of the processor in a case where a difference between the current recognition result of the processor and information corresponding to a recognition result of the processor specified from information related to past radiographic imaging is equal to or greater than a threshold value, and determines the second position used in current radiographic imaging using information related to past radiographic imaging in a case where the difference is less than the threshold value.

17. A radiographic imaging system, comprising:

a radiographic imaging apparatus body disposed in an imaging room and having radiation generation unit that generates radiation, a radiographic imaging unit that images a subject using the radiation, and a movable unit that movably supports the radiation generating unit and the radiographic imaging unit;

a camera that captures an image of the subject by using light other than the radiation; and a processor configured to:

acquire subject information regarding the subject;

perform a first position control in which a position of the movable unit is automatically moved to a first position according to a physique of the subject using the subject information;

recognize the subject using the image of the subject captured by the camera; and perform a second position control in which the position of the movable unit is moved from the first position to a second position automatically according to the recognition result, wherein the processor recognizes an examination technician who uses the radiographic imaging apparatus body so as to be distinguished from the subject.

* * * * *